United States Patent
Tomita et al.

(10) Patent No.: US 6,932,807 B1
(45) Date of Patent: Aug. 23, 2005

(54) LASER TREATMENT APPARATUS

(75) Inventors: Seiki Tomita, Gamagori (JP); Shinichi Matsuura, Gamagori (JP); Yasuyuki Naito, Nukata-gun (JP)

(73) Assignee: Nidek Co., Ltd., Gamagori (JP)

( * ) Notice: Subject to any disclaimer, the term of this patent is extended or adjusted under 35 U.S.C. 154(b) by 118 days.

(21) Appl. No.: 09/648,547

(22) Filed: Aug. 28, 2000

(30) Foreign Application Priority Data

Sep. 1, 1999 (JP) ................................. 11-247192
Sep. 29, 1999 (JP) ................................. 11-276481

(51) Int. Cl.$^7$ ............................................. A61F 9/008
(52) U.S. Cl. ............................... 606/10; 606/4; 606/13
(58) Field of Search ............................ 606/3–6, 10–14

(56) References Cited

U.S. PATENT DOCUMENTS

| | | | |
|---|---|---|---|
| 4,638,801 A * | 1/1987 | Daly et al. ................. | 606/4 |
| 4,907,586 A * | 3/1990 | Bille et al. ................. | 606/5 |
| 5,048,946 A * | 9/1991 | Sklar et al. ................ | 606/4 |
| 5,076,685 A | 12/1991 | Muller et al. | |
| 5,098,426 A * | 3/1992 | Sklar et al. ................ | 606/13 |
| 5,177,511 A | 1/1993 | Feuerstein et al. | |
| 5,285,223 A | 2/1994 | Ueno et al. | |
| 5,364,390 A * | 11/1994 | Taboada et al. ........... | 606/10 |
| 5,439,462 A * | 8/1995 | Bille et al. ................. | 606/6 |
| 5,488,443 A | 1/1996 | Ota et al. | |
| 5,537,163 A | 7/1996 | Ueno | |
| 5,644,375 A | 7/1997 | Suzuki | |
| 5,688,262 A * | 11/1997 | Abraham .................. | 606/18 |
| 5,980,513 A * | 11/1999 | Frey et al. ................. | 606/10 |

FOREIGN PATENT DOCUMENTS

| | | |
|---|---|---|
| EP | 0293126 A 1 | 11/1988 |
| JP | 64-500009 | 9/1987 |
| JP | 6-90907 | 4/1994 |
| JP | 6-154265 | 6/1994 |
| JP | 7-67909 | 3/1995 |
| JP | 8-299280 | 11/1996 |
| JP | 2000-135238 | 5/2000 |

* cited by examiner

Primary Examiner—David M. Shay
(74) Attorney, Agent, or Firm—Oliff & Berridge, PLC

(57) ABSTRACT

A laser treatment apparatus for irradiating an affected part of a patient's eye with a treatment laser beam to treat the affected part is disclosed. The laser treatment apparatus includes treatment beam irradiation section including a first irradiation optical system for irradiating the treatment beam; aiming beam irradiation section including a second irradiation optical system for irradiating an aiming beam, the second irradiation optical system being optically adjusted such that sighting of the treatment beam is completed when the aiming beam forms a predetermined shape on a reflection plane; image pickup section including an image pickup optical system for imaging an area including the affected part of the patient's eye; sighting detection section for processing an image of the aiming beam picked-up by the image pickup section to detect a sighting state; movement detection section for detecting movement in an optical axis direction of at least one of at least a part of the image pickup optical system and at least a part of the irradiation optical system; and determination section for determining a direction in which at least one of at least the part of the image pickup optical system and at least the part of the irradiation optical system is to be moved based on results detected by the sighting detection section and the movement detection section respectively.

11 Claims, 10 Drawing Sheets

LASER TREATMENT APPARATUS

BACKGROUND OF THE INVENTION

1. Field of the Invention

The present invention relates to a laser treatment apparatus for irradiating an affected part of a patient's eye with a treatment laser beam.

2. Description of Related Art

For treatment for aftercataract and so on of a patient's eye, there conventionally has been used a laser treatment apparatus (laser operation equipment) for irradiating an affected part of the patient's eye with a treatment laser beam of pulse wave. The apparatus of this kind is designed to vaporize and crush the tissue of the affected part by focusing the treatment laser beam on a desired point (an area to be treated) of the affected part, thereby forming plasma to generate shock waves. Accordingly, the importance is to precisely focus the treatment laser beam on the desired point. For achieving this purpose, there has been known a method of focusing a treatment laser beam on a desired point after irradiating two (or more) visible aiming beams so as to coincide with each other (i.e., to overlap two images of the aiming beams) at the desired point on which the treatment laser beam is to be focused. It is to be noted that the coincidence of two aiming beams at the desired point for the focusing of the treatment laser beam on the desired point is referred hereinafter to as "sighting".

Moreover, there is a method of shifting a focus point of the treatment laser beam to the coincident point of the aiming beams. In this case, the sighting is also important.

For treatment for retinal diseases, there has been used a laser treatment apparatus (photocoagulation apparatus) for irradiating an affected part of a patient's eye with a treatment laser beam of continuous wave. The apparatus of this type is designed so that a visible aiming beam is irradiated to focus on a desired point which is the same as a focus point of the treatment laser beam to form an image with the minimum spot diameter, whereby the treatment laser beam is precisely focused on the desired point. It is also noted that the focusing of the aiming beam on the desired point to ensure the focusing of the treatment laser beam thereon is also referred to as "sighting".

The sighting, however, is performed by an operator while observing the coincident state of the two aiming beams (the overlapping condition of the two images of the aiming beams) or the focusing condition of the aiming beam (the spot diameter of the image of the aiming beam) through eyepieces of a microscopic section of the apparatus. This would cause a difficulty for low-skilled operators in judging the propriety of the sighting. Furthermore, differences among operators may be included in determinations about the propriety of the sighting.

During treatment, for example, during sighting of the aiming beams or irradiating of the treatment laser beam, the operator has to observe the patient's eye through the eyepieces of the microscopic section while holding a contact lens by one hand on the patient's eye. Thus, some operators who are for example of short stature must operate and observe in a forced or uncomfortable position.

SUMMARY OF THE INVENTION

The present invention has been made in view of the above circumstances and has an object to overcome the above problems and to provide a laser treatment apparatus which allows an operator to easily observe a patient's eye and to precisely easily perform sighting in order to focus a treatment laser beam on a desired point.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a laser treatment apparatus for irradiating an affected part of a patient's eye with a treatment laser beam to treat the affected part, including: treatment beam irradiation means including a first irradiation optical system for irradiating the treatment beam; aiming beam irradiation means including a second irradiation optical system for irradiating an aiming beam, the second irradiation optical system being optically adjusted such that sighting of the treatment beam is completed when the aiming beam forms a predetermined shape on a reflection plane; image pickup means including an image pickup optical system for imaging an area including the affected part of the patient's eye; sighting detection means for processing an image of the aiming beam picked-up by the image pickup means to detect a sighting state; movement detection means for detecting movement in an optical axis direction of at least one of at least a part of the image pickup optical system and at least a part of the irradiation optical system; and determination means for determining a direction in which at least one of at, least the part of the image pickup optical system and at least the part of the irradiation optical system is to be moved based on results detected by the sighting detection means and the movement detection means respectively.

It is preferable that the laser treatment apparatus further includes observation means including a display for displaying an image picked up by the image pickup means on the display.

It is preferable that the laser treatment apparatus further includes display control means for causing the display to display that the sighting state is proper based on the result detected by the sighting detection means.

It is further preferable that the laser treatment apparatus further includes display control means for causing the display to display the direction in which at least one of at least the parts of the image pickup optical system and the irradiation optical system are to be moved based on the result detected by the determination means.

Preferably, in the laser treatment apparatus the display is place-changeably mounted on the apparatus.

It is preferable that the laser treatment apparatus further includes movement means for automatically moving at least one of at least the part of the image pickup optical system and at least the part of the irradiation optical system based on the result detected by the determination means.

It is preferable that the laser treatment apparatus further includes: movement means for automatically moving at least one of at least the part of the image pickup optical system and at least the part of the irradiation optical system; and movement control means for controlling the movement means to move at least one of at least the part of the image pickup optical system and at least the part of the irradiation optical system by a predetermined amount in a predetermined direction based on an instruction to start automatic sighting.

Preferably, in the laser treatment apparatus the aiming beam irradiation means irradiates a plurality of aiming beams which are symmetrical about an optical axis to coincide with each other at a focus point of the treatment laser beam, and the sighting detection means detects the sighting state based on an overlapping condition of the images of the plurality of aiming beams.

Preferably, in the laser treatment apparatus the aiming beam irradiation means irradiates the aiming beam to focus on a focus point of the treatment laser beam, and the sighting detection means detects the sighting state based on a spot diameter of the image of the aiming beam.

Preferably, in the laser treatment apparatus the treatment beam irradiation means includes a laser source which emits a YAG laser beam as the treatment laser beam.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

A detailed description of preferred embodiments of a laser treatment apparatus embodying the present invention will now be given referring to the accompanying drawings.

FIG. 1 is a schematic perspective view of the laser treatment apparatus (YAG laser operation apparatus) in the first embodiment according to the present invention.

Numeral 1 is a main unit of the apparatus for emitting a treatment laser beam (which is hereinafter simply referred to as a treatment beam) of pulsed wave. This main unit 1 is internally provided with a treatment laser source, an aiming laser source, a light delivery optical system, a controller, and others. Numeral 2 is a stand with a table which is movable up and down, on which the main unit 1 is mounted. Numeral 4 is a joystick used for moving the main unit 1 on the table of the stand 2 in a back-to-front and right-to-left directions.

The joystick 4 is provided at its upper portion with a rotating knob which is used for moving the main unit 1 up and down. The moving mechanism of the main unit 1 by means of the joystick and the rotating knob are well known, of which explanation is therefore omitted. The joystick 4 is also provided at its top portion with a trigger switch 4a for generating an instruction signal to start emission of the treatment beam. Numeral 3 is a control panel used for setting laser irradiation conditions such as the number of pulses of the treatment beam, the power of the same, and the luminous intensity of an aiming laser beam (which is hereinafter simply referred to as an aiming beam), and others.

Figure 1A:
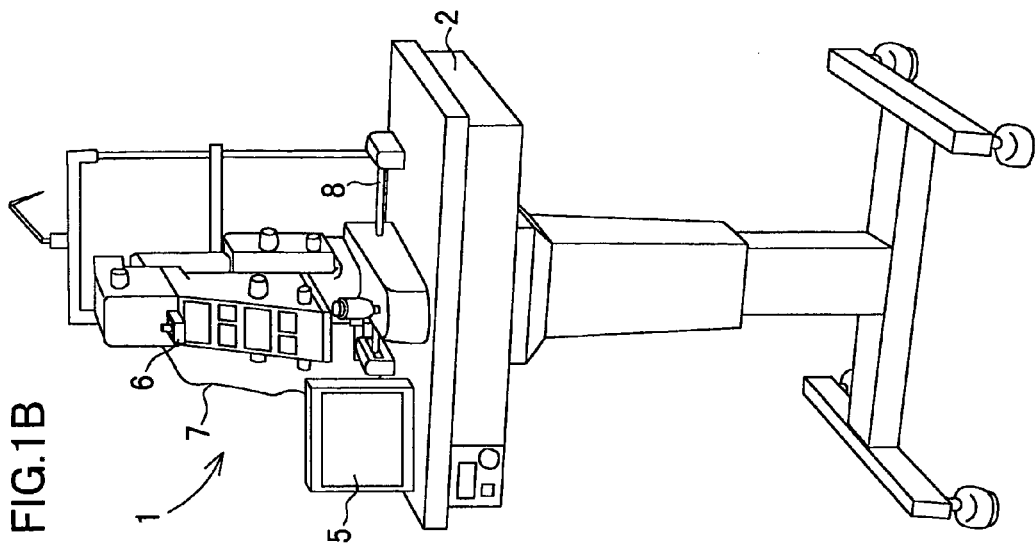
FIGS. 1A and 1B are schematic perspective views of a laser treatment apparatus in a first embodiment according to the present invention.
Figure 1B:
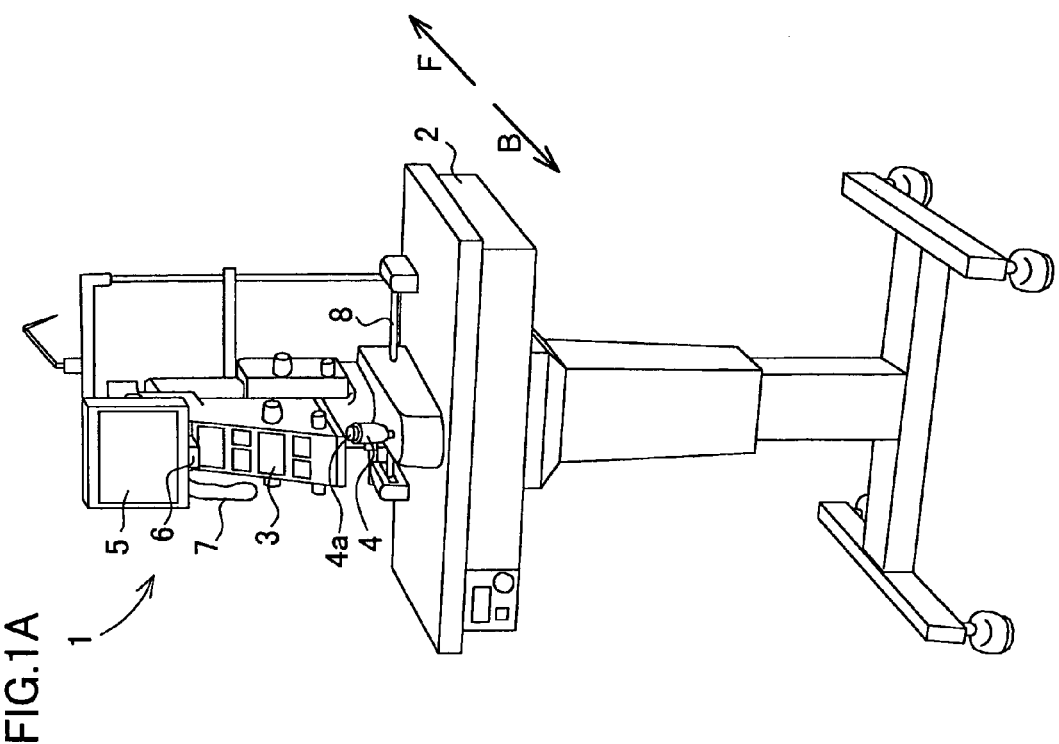

Numeral 5 is a display for displaying information (data) transmitted from a CCD camera 26 and a controller 30 (which will be mentioned later) through a cable 7. This display 5 is attached on a rack 6 fixedly provided to the main unit 1 as shown in FIG. 1A, and is removable from the rack 6 as shown in FIG. 1B. The display 5 can thus be used in any place where an operator wishes.

Figure 2:
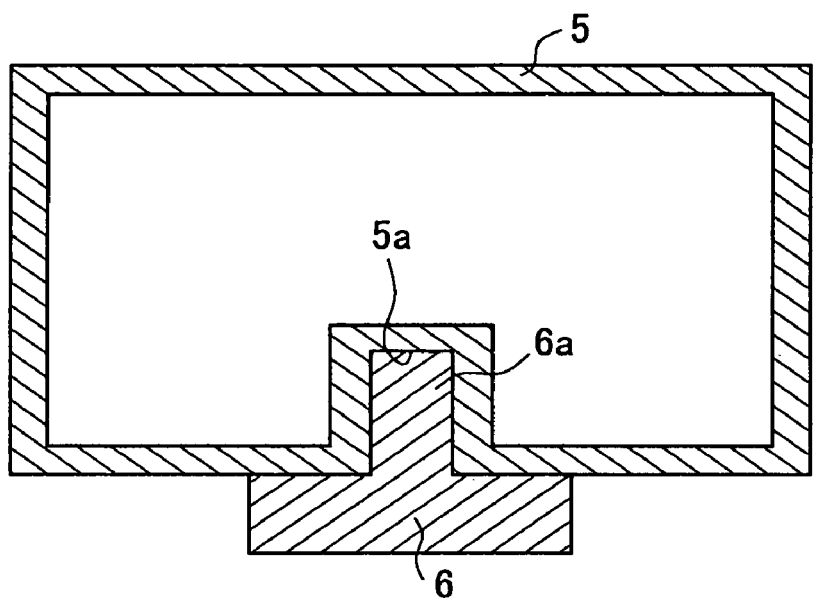
FIG. 2 is a schematic sectional view of a mechanism for mounting a display on a main unit in the first embodiment.

The display 5 is attached on the rack 6 under the condition that a support shaft 6a of the rack 6 is inserted in a hole 5a of the display 5 as shown in FIG. 2. The display 5 is rotatable about the support shaft 6a.

Figure 3:
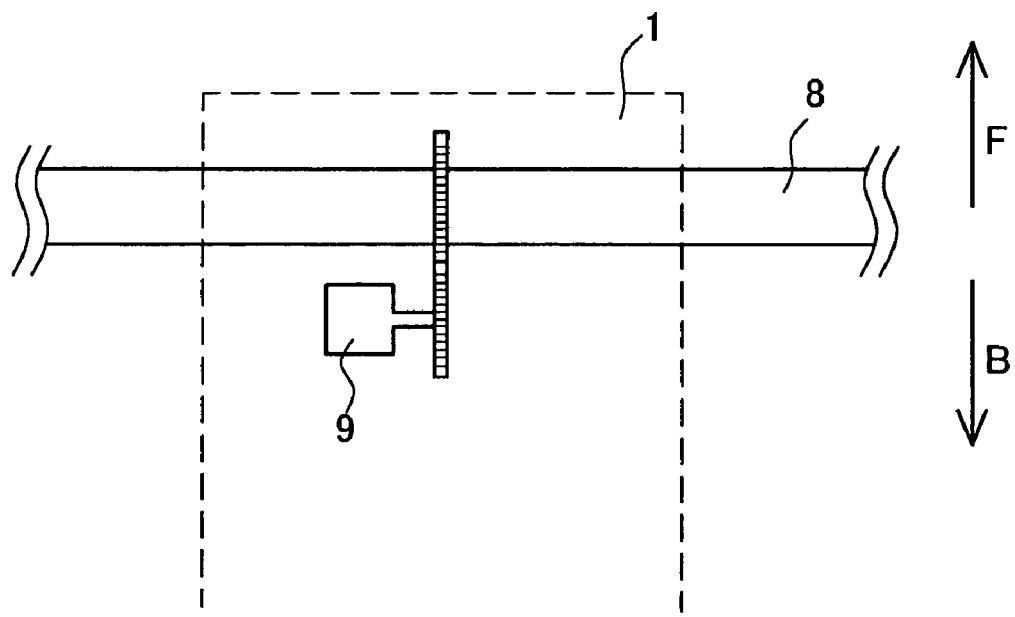
FIG. 3 is a schematic structural view of a mechanism for detecting moving directions of the main unit.

Numeral 8 is an axle for moving the main unit 1 in a forward (an arrow F in FIGS. 1A and 3) direction and a backward (an arrow B) direction. As shown in FIG. 3, in the main unit 1 a potentiometer 9 is attached on the axle 8 through gears, whereby to allow detection of a moving direction (and also a moving amount) of the main unit 1 on the basis of a rotating direction of the axle 8 (and also a rotating amount). Information (data) on a detected moving direction (and also a moving amount) is used in a sighting operation for focusing of the treatment beam.

Figure 4:
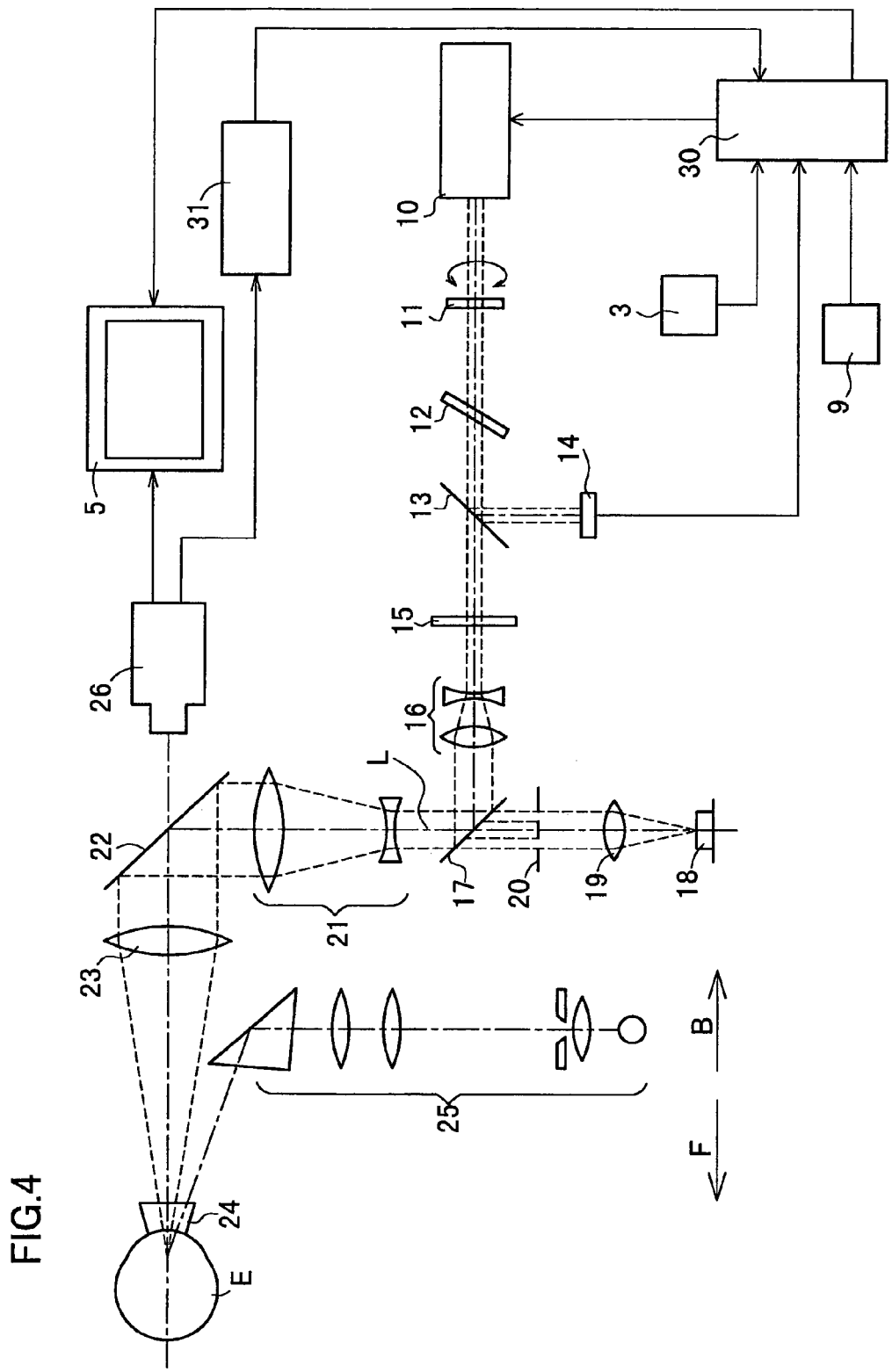
FIG. 4 is a schematic structural view of an optical system and a control system of the apparatus in the first embodiment.

FIG. 4 is a schematic structural view of an optical system and a control system of the apparatus in the first embodiment. Numeral 10 is a Nd:YAG laser serving as a treatment laser source which emits a treatment beam having a dominant wavelength of 1064 nm. Numeral 11 is a half-wavelength plate for rotating the direction of polarization of the treatment beam. Numeral 12 is a polarizing filter placed at the Brewster angle. The wavelength plate 11 is rotated by operation of an energy adjusting knob not shown to adjust the power of the treatment beam to be irradiated to the affected part in combination with the polarizing filter 12. Numeral 13 is a beam splitter. A part of the treatment beam passed through the polarizing filter 12 is reflected by the beam splitter 13 to enter a power sensor 14 which detects the power of the treatment beam.

Numeral 15 is a safety shutter serving to intercept the treatment beam when inserted on the beam path in a predetermined case for example of an oscillation test or occurrence of an abnormal event. While the shutter 15 is out of the beam path, the treatment beam being not intercepted by the shutter 15 is expanded by a group of expander lenses 16. The treatment beam is then reflected by a dichroic mirror 17 to made coaxial with the aiming beam (which is a red light having a dominant wavelength of 633 nm) emitted from a semiconductor laser 18 serving as an aiming laser source. The aiming beam emitted from the laser source 18 is made into parallel luminous flux by a lens 19 and split into two beams by an aperture 20 having two openings formed symmetrically with respect to an optical axis L.

Numeral 21 is a group of expander lenses for expanding each luminous flux of the treatment beam and the aiming beam. Numeral 22 is a dichroic mirror which reflects most of the treatment beam and the aiming beam, while transmitting an observation light, whereby to make the optical axis L coaxial with the optical axis of an objective lens 23. The treatment beam, after reflected by the dichroic mirror 22, is focused on a point near the affected part of the patient's eye E through the objective lens 23 and a contact lens 24. The two split aiming beams are reflected by the dichroic mirror 22 and coincide with each other at a reference focus point of the treatment beam. The focus point of the treatment beam may be shifted with respect to the coincident point of the aiming beams by movement of the expander lenses 16 in the optical axis direction.

Numeral 25 is a slit light projecting optical system. The slit light from the projecting optical system 25 is delivered to illuminate the eye E through the contact lens 24.

Numeral 26 is a CCD camera for receiving the reflection light from the eye E. The image picked-up by the CCD camera 26 is displayed on the display 5.

Numeral 30 is a controller for controlling the whole apparatus. Numeral 31 is an image processing section for processing the images of the two aiming beams picked-up by the camera 26 to detect the overlapping condition of the images.

Next, explanation is made on a method of detecting the overlapping condition (coincident state) of the images of the aiming beams by image processing, referring to FIG. 5. FIG. 5 is an explanatory view of the method of detecting the overlapping condition of the aiming beams by extracting only the images of the aiming beams and its surrounding area picked-up by the camera 26.

In FIG. 5, numerals 50a and 50b denote the images of the two split aiming beams irradiated in two directions to the eye E. For example, they are the images of the aiming beams reflected at the desired point (the area to be treated) such as a point in posterior capsule and picked-up by the camera 26.

Figure 5A:
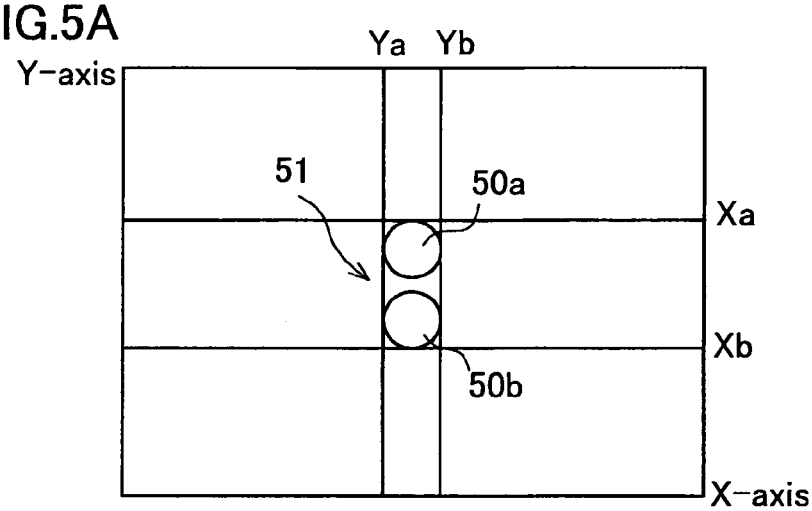
FIGS. 5A, 5B, and 5C are explanatory views of showing a method of detecting a coincident state of aiming beams by image processing.

The image processing is executed in the following manner. The image processing section 31 first extracts the images 50a and 50b of the aiming beams based on a difference in light quantity with respect to the surroundings in the image data coming from the camera 26. Sequentially, a straight line Xa is created to come in contact with the uppermost end of the extracted images of the aiming beams (which is an upper end of the image 50a of the aiming beam in the present embodiment) and to be parallel with an X-axis, and another straight line Xb is created to come in contact with the lowermost end of the images (which is an lower end of the image 50b in the present embodiment) and to be parallel with the X-axis, as shown in FIG. 5A. Similarly, a straight line Ya is created to come in contact with the leftmost end of the images (which is a left end of either one of the images 50a and 50b) and to be parallel with a Y-axis, and another straight line Yb is created to come in contact with the rightmost end of the images (which is a right end of either one of the images 50a and 50b) and to be parallel with the Y-axis.

Figure 5B:
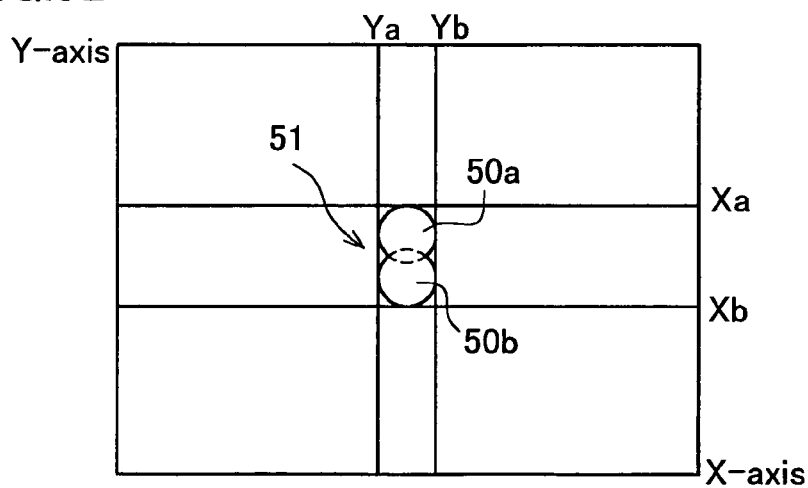
Figure 5C:
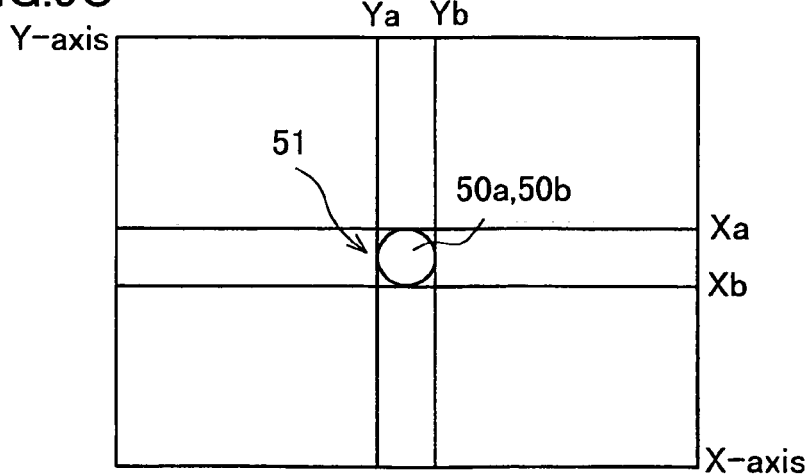

The straight lines Xa, Xb, Ya, and Yb created as above define a rectangle region 51. This region 51 changes in area depending on an overlapping condition of the two images of the aiming beams, namely, a coincident state of those images. To be more specific, when the images 50a and 50b come close to each other to overlap (coincide with) each other as shown in FIG. 5B from the state in FIG. 5A, the area of the region 51 is reduced. When the region 51 is reduced to the minimum area where the images 50a and 50b of the aiming beams are completely overlapped each other on the treatment area as shown in FIG. 5C, the image processing section 31 determines that sighting to the treatment area is completed, namely, that the sighting point is proper.

Operation of the laser treatment apparatus having the above configuration will be explained below.

At first, using the control panel 3, an operator sets laser irradiation conditions such as the power of the treatment beam and others. The controller 30 then causes the display 5 to display the set laser irradiation conditions as setting information 53 in a lower part on the display 5 (see FIG. 6). With the laser irradiation conditions displayed on the display 5, the operator can confirm the laser irradiation conditions without the need of directly viewing the main unit 1 side (the control panel 3).

The operator may place the display 5 in an easy-to-see place in consideration of treatment using the contact lens 24. By the operation of the joystick 4, the operator moves the main unit 1 until the image of the eye E appears on the display 5.

Figure 6A:
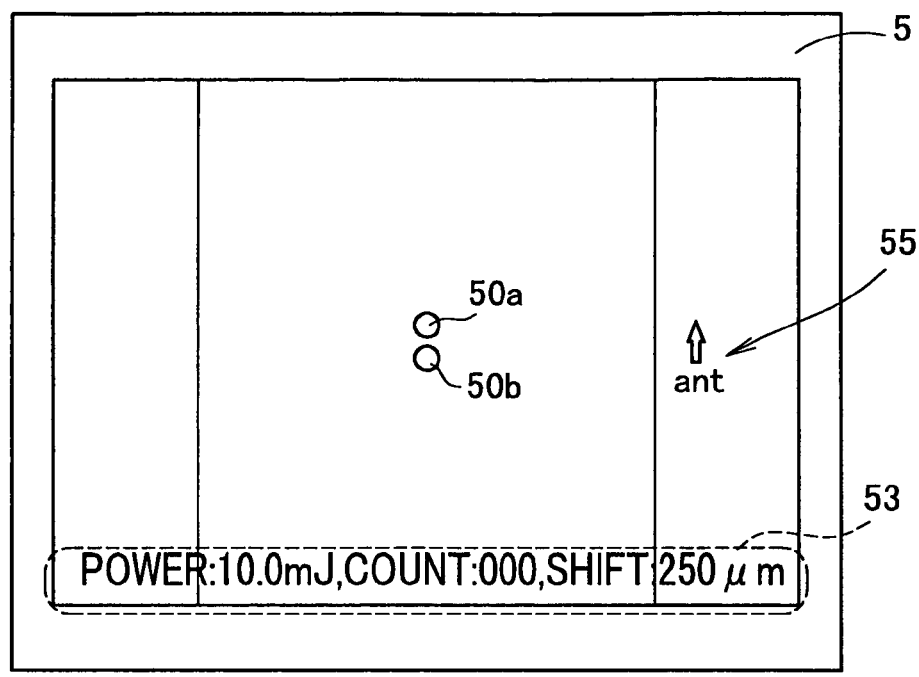
FIGS. 6A and 6B are examples of a screen appearing on the display.
Figure 6B:
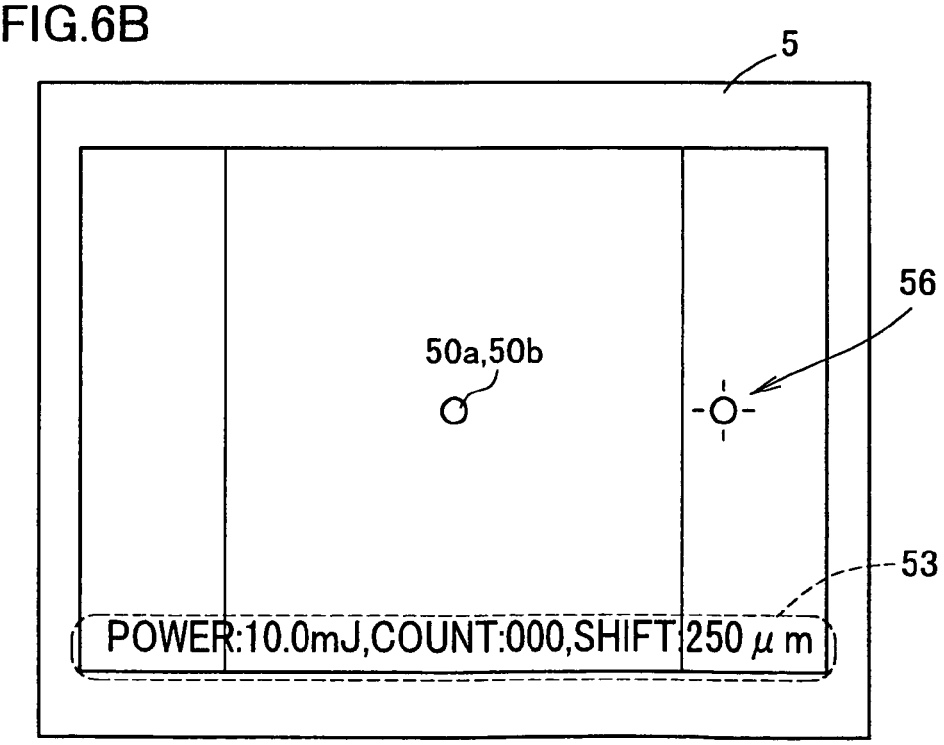

As shown in FIG. 6A, on the display 5 the two images of the aiming beams reflected by the treatment area come to appear. The operator further operates the joystick 4 to slightly move the main unit 1 so that the images 50a and 50b of the aiming beams overlap each other. The image processing section 31 detects the overlapping condition (the coincident state) of the images 50a and 50b by the image processing at all times to transmit the image information (data) to the controller 30.

Simultaneously the potentiometer 9 transmits the movement information (data) on the movement of the main unit 1 to the controller 30. The controller 30 causes the display 5 to display the information (data) on the coincident state of the aiming beams with respect to the treatment area based on the image information (data) coming from the image processing section 31 and the movement information (data) coming from the potentiometer 9 respectively.

For example, when the coincident point of the aiming beams is at an operator's side (in the direction B), the main unit 1 should be moved forward (in the direction F), whereby the region 51 shown in FIG. 5A is reduced in area. The controller 30 can find the deviation direction of the coincident point of the aiming beams (i.e., the focus point of the treatment beam) with respect to a proper sighting point based on the information (data) on the moving direction of the main unit 1 from the potentiometer 9 and the information (data) on the changes in area of the region 51 (which is the information on the overlapping condition of the images of the aiming beams). When the deviation direction of the coincident point is at the operator's side with respect to the proper sighting point, the controller 30 causes the display 5 to display an "ant" sign representing that effect and an arrow mark 55 indicating the direction in which the main unit 1 should be moved. The operator, viewing the displayed information, operates the joystick 4 to move the main unit 1 forward. In further sighting, the images 50a and 50b of the aiming beams come to overlap each other on the treatment area, resulting in difficulty in recognizing them with the naked eye of the operator. However, the operator can perform the sighting based on the information displayed on the display 5.

When the image processing section 31 detects that the images 50a and 50b of the aiming beams are overlapped each other into one image (or enter in a predetermined acceptable range), the controller 30 causes the display 5 to display an "OK" sign and a mark 56 indicating that the sighting is the most proper. When that sign appears on the display 5, the operator stops the sighting and depresses the trigger switch 4a to start irradiation of the treatment beam to the treatment area.

In the above manner, the sighting can be executed based on the information (data) produced by the image processing, so that the operator can properly perform the sighting even if the coincident state of the aiming beams is difficult for the operator to recognize.

In the present embodiment, the control panel 3 is used to set the laser irradiation conditions, but it is not limited thereto. The display 5 may be configured in a touch panel type so as to allow the operator to set the laser irradiation condition with a touch of the screen of the display 5.

Figure 7:
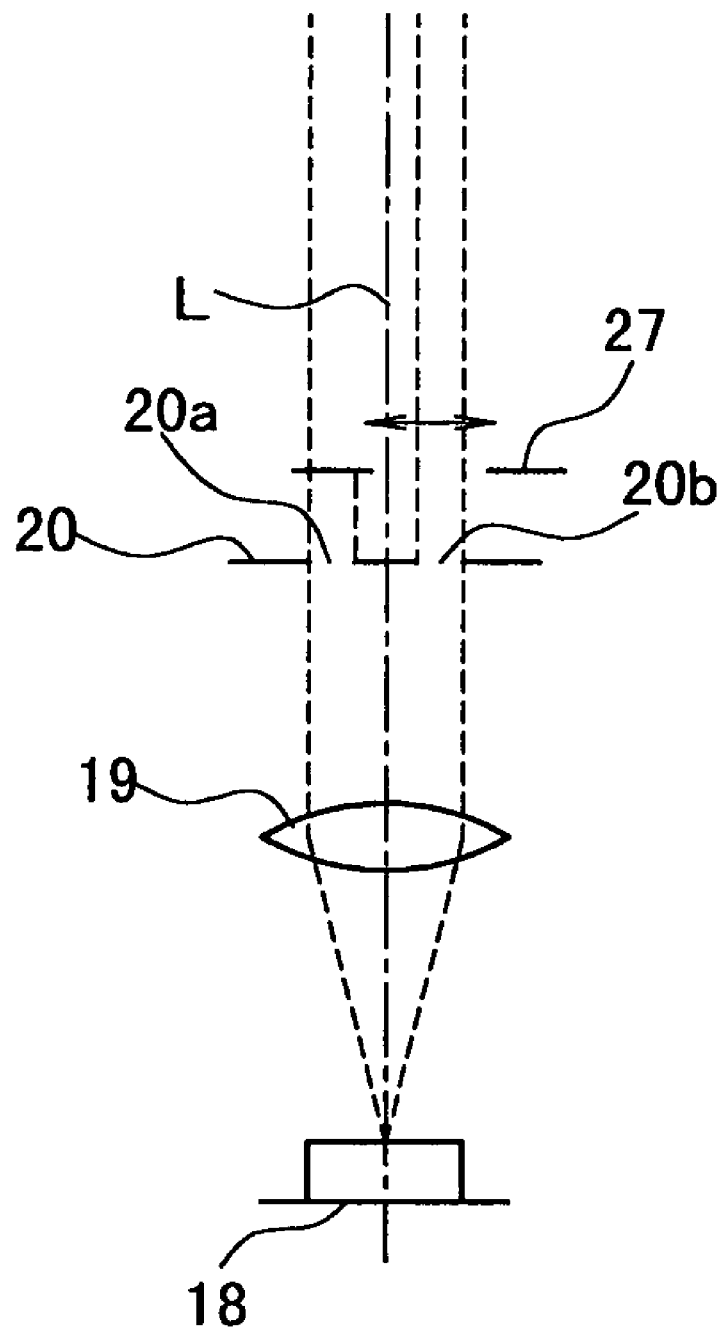
FIG. 7 is an explanatory view of showing a method of finding a deviation direction of the aiming beams.

The deviation direction of the coincident point of the aiming beams (the focus point of the treatment beam) can also be found in the following manner. As shown in FIG. 7, a shutter 27 is provided to alternately open the openings 20a and 20b of the aperture 20. Under control of the controller 30, the shutter 27 is driven to alternately allow irradiation of the two aiming beams. Based on the information (data) on the images 50a and 50b of the aiming beams by the image processing and the information (data) on opening/closing of the shutter 27, the controller 30 determines the deviation direction of the coincident point of the aiming beams and the propriety as to whether the sighting is proper. To be more specific, when the coincident point is deviated to the operator's side (in the direction B), the opening 20a is opened to allow irradiation of the aiming beam, whereby the image 50a shown in FIG. 5A is detected. When the opening 20b is opened, the image 50b is detected. On the other hand, when the coincident point is deviated to the rear side (in the direction F), the detected image is opposite to above. Thus, the deviation direction in relation to the coincident point can be found; the operator's side or the rear side. Alternatively, the propriety of the sighting can be determined according to whether the distance between the centers of the images 50a and 50b of the aiming beams is within a predetermined acceptable range.

Figure 8:
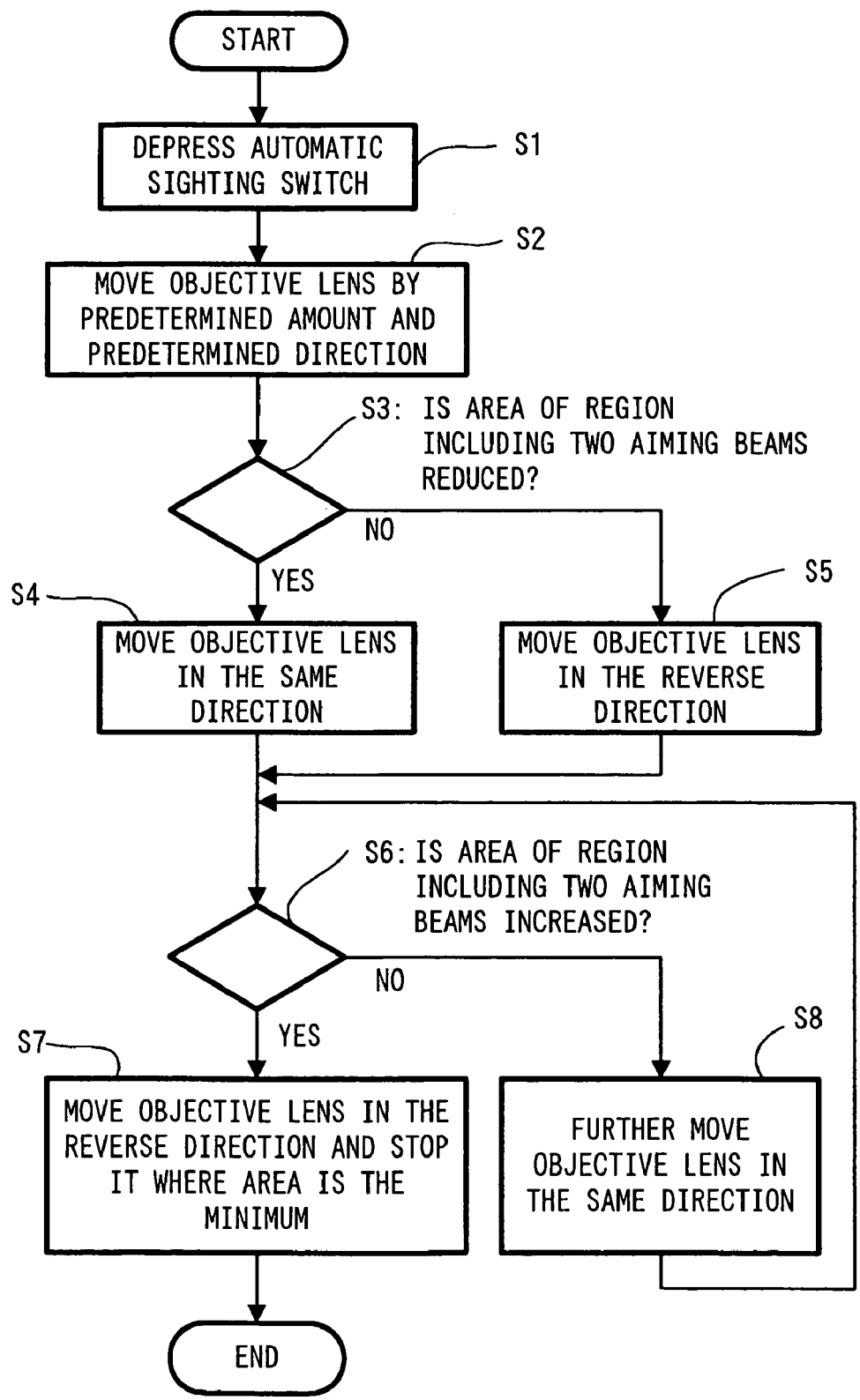
FIG. 8 is a flowchart of showing a routine of automatic sighting in the first embodiment.

Utilizing the above information, the sighting also can be executed automatically (see FIGS. 5 and 8). Upon depression of an automatic sighting switch not shown of the control panel 3 (S1), the controller 30 drives a lens driving section not shown consisted of motors and cams to move the lens 23 by a predetermined amount in a predetermined direction (which may be either direction of the optical axis) (S2). If the region 51 is reduced in area in association of the movement of the lens 23 in the predetermined direction (S3: YES), the lens 23 is further moved in the same direction as the predetermined direction (S4). When the area of the region 51 comes to increase past the minimum (S6: YES), the lens 23 is moved in the reverse direction to reduce the area of the region 51. The lens 23 is then stopped when the region 51 is reduced to the minimum area (S7). If NO in S6, on the other hand, the lens 23 is further moved in the same direction as in S4 (S8).

If the moving direction and the moving amount of the lens 23 are stored in the controller 30 in relation to the information (data) detected by the image processing, the lens 23 can be easily returned to the position where the area of the region 51 reaches the minimum.

On the other hand, if the region 51 is increased in area when the lens 23 is moved in the predetermined direction (S3: NO), the lens 23 is moved in the reverse direction to reduce the area of the region 51 (S5). Then, when the area of the region 51 comes to increase (S6: YES), the lens 23 is moved in the reverse direction to in S5 and is stopped when the region 51 is reduced to the minimum area (S7). If No in S6, the lens 23 is further moved in the same direction as in S5 (S8).

Upon stop of the lens 23 (completion of the sighting), the OK sign and the mark 56 are displayed on the display 5. Viewing the displayed information, the operator stops the sighting and depresses the trigger switch 4a to start irradiation of the treatment beam to the treatment area.

In the case where the two aiming beams are alternately irradiated as shown in FIG. 7, similarly, the deviation direction of the coincident point of the aiming beams and the propriety of the sighting can be determined based on the information (data) on the images 50a and 50b of the aiming beams by the image processing and the information (data) on opening/closing of the shutter 27, thus enabling the automatic sighting.

In the automatic sighting, the apparatus may be arranged to automatically irradiate the treatment beam after completion of the sighting, where the trigger switch 4a may be omitted. It may also be arranged to preclude laser irradiation until the sighting is completed by inserting the shutter 15 in the beam path. The same goes for the manual sighting mentioned above.

Although the automatic sighting is conducted by movement of the lens 23 in the optical axis direction in the above embodiment, the sighting may be conducted by automatic movement of the main unit 1 caused by means of a mechanism for electrically moving the main unit 1 forward and backward based on the information and others by the image processing.

To the contrary, the manual sighting may be executed by movement of the lens 23 by operation of a knob not shown instead of movement of the main unit 1 by operation of the joystick 4.

It is needless to say that the automatic sighting is effective in a conventional laser treatment apparatus provided with a microscope.

Figure 9:
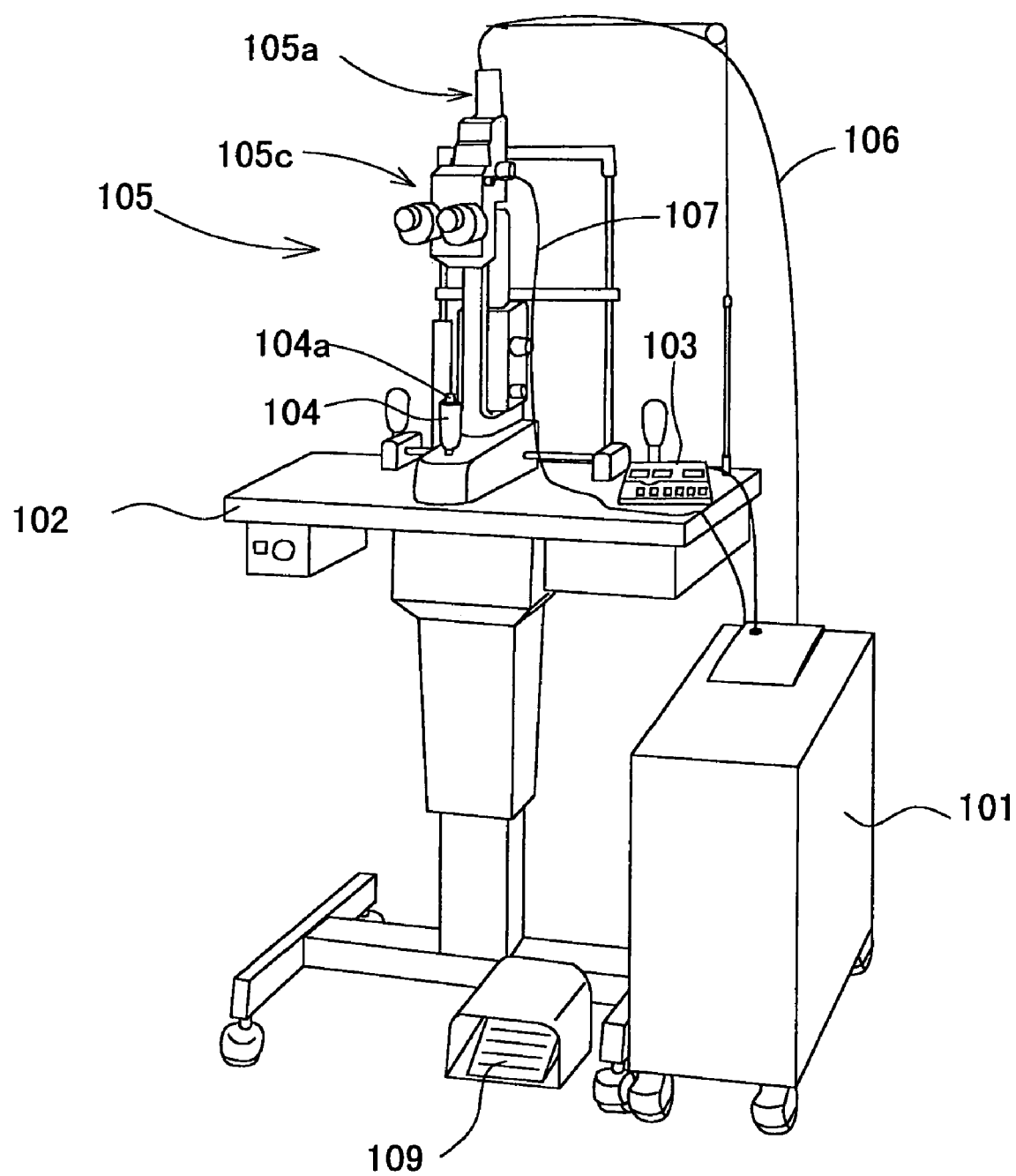
FIG. 9 is a schematic perspective view of a laser treatment apparatus in a second embodiment according to the present invention.

Next, a second embodiment according to the present invention will be described. FIG. 9 is a schematic perspective view of a laser treatment apparatus (Green-YAG laser photocoagulation apparatus) in the second embodiment.

Numeral 101 is a main unit of the laser treatment apparatus for emitting a treatment laser beam of continuous wave (which is hereinafter simply referred to as a treatment beam). The main unit 101 is internally provided with a treatment laser source, an aiming laser source, a light delivery optical system, and a controller, and others. Numeral 102 is a stand movable up and down. Numeral 104 is a joystick (and a rotating knob) used for moving the main unit 101 and is provided at its top with a trigger switch 104a for generating an instruction signal of emission of the treatment beam. Numeral 103 is a control panel used for setting laser irradiation conditions such as the power and the number of pulses of the treatment beam, the luminous intensity of a laser beam for aiming (which is hereinafter simply referred to as an aiming beam).

Numeral 105 is a slit-lamp delivery unit for irradiating the treatment beam to an affected part of a patient's eye E while allowing an operator to observe the affected part. The slit-lamp delivery unit 105 is essentially consisted of a laser irradiation section 105a internally provided with an irradiation optical system 140, an illumination section 105b internally provided with an illumination optical system 125, and a microscopic section 105c internally provided with an observation optical system 150. Numeral 107 is a cable for transmitting the image information (data) from a CCD camera 126 included in the observation optical system 150 to the main unit 101.

Numeral 109 is a foot switch serving as a trigger switch used for generating an instruction signal of emission of the treatment beam.

Figure 10:
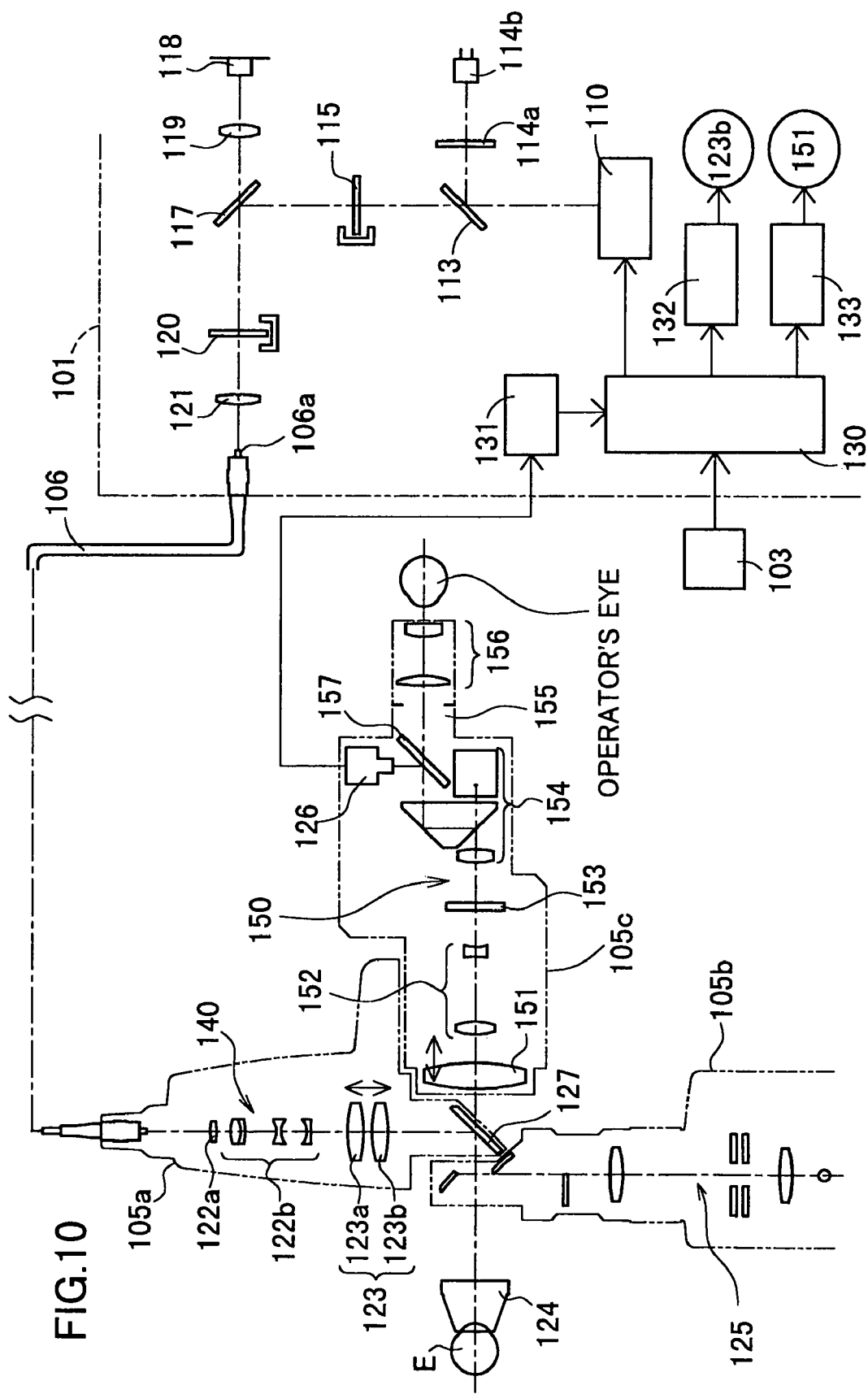
FIG. 10 is a schematic structural view of an optical system and a control system of the apparatus in the second embodiment.

FIG. 10 is a schematic structural view of an optical system and a control system of the apparatus in the second embodiment. Numeral 110 is a laser source which is an Nd:YAG laser capable of oscillating a fundamental wavelength of 1064 nm. In the present embodiment, the laser source 110 generates a green treatment beam of 532 nm (linearly polarized light) which is double the fundamental wavelength. A part of the treatment beam emitted from the laser source 110 is reflected by a beam splitter 113 and, after passing through a diffusing plate 114a, is detected by a power sensor 114b.

Numeral 115 is a first safety shutter for intercepting the treatment beam. Numeral 117 is a dichroic mirror for reflecting the treatment beam to make it coaxial with the aiming beam (which is a red light of a dominant wavelength of 633 nm) from a semiconductor laser 118 serving as an aiming laser source. Numeral 119 is a collimator lens and numeral 120 is a second safety shutter which is inserted in the beam path while the aiming laser source 118 does not emit the aiming beam. When the shutter 120 is moved out of the beam path, the treatment beam and the aiming beam are allowed to pass without interception by the shutter 120 and are converged by a focusing lens 121 into an entrance 106a of an optical fiber 106.

Numeral 140 is an irradiation optical system in the laser irradiation section 105a. The treatment beam and the aiming beam delivered to the system 140 through the fiber 106 pass through a relay lens 122a, a group of zoom lenses 122b movable in the optical path for changing a spot diameter of the beams, and an objective lens 123. The beams are then reflected by a movable mirror 127 to irradiate the affected part of the eye E through a contact lens 124. The objective lens 123 is structured of a fixed lens 123a and a movable lens 123b. Moving the movable lens 123b in the optical axis direction executes a minute sighting.

Numeral 125 is a slit-light projecting optical system in the illumination section 105b. The slit light from this system 125 illuminates the eye E through the contact lens 124.

Numeral 150 is an observation optical system in the microscopic section 105c. This microscopic section 105 is designed for binocular observation and provided with a pair of the observation optical systems 150, though only one of the systems 150 is shown in FIG. 10. The observation optical system 150 includes an objective lens 151, a group of variable magnification lenses 152, a protective filter 153, a group of erect prisms 154, a field diaphragm 155, and eyepieces 156. A half mirror 157 is disposed between the erect prisms 154 and the field diaphragm 155 on either one of binocular observation optical paths. The light reflected by the half mirror 157 is received by a CCD camera 126.

Numeral 130 is a controller for controlling the whole apparatus. Numeral 131 is an image processing section for processing the image of the aiming beam picked-up by the camera 126 to detect a forming state (a spot diameter) of the image.

It is to be noted that the lens 123b and the lens 151 are moved interlockingly on respective optical axes by means of corresponding lens driving sections 132 and 133.

Figure 11:
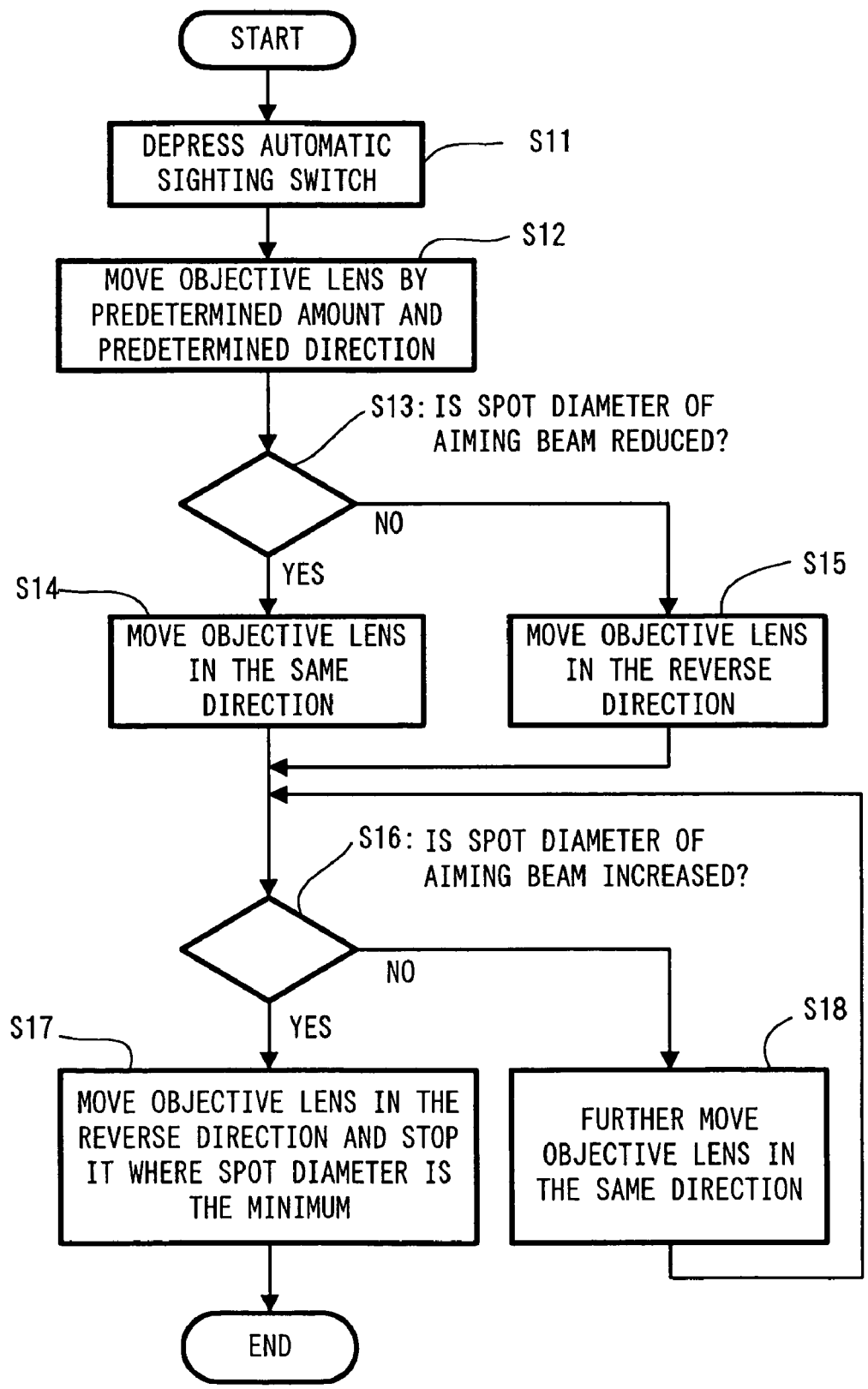
FIG. 11 is a flowchart of showing a routine of automatic sighting in the second embodiment.

Next, explanation is made on a method for executing automatic sighting based on image processing, referring to a flowchart in FIG. 11. To focus the aiming beam on the same point as the treatment beam, the sighting is conducted such that the spot diameter of the aiming beam reflected at a desired point (the treatment area) is reduced to the minimum.

Upon depression of an automatic sighting switch not shown on the control panel 103 (S11), the image processing section 131 extracts the image of the aiming beam based on a difference in light quantity with respect to the surroundings in the image data transmitted from the camera 126 to detect the spot diameter of the aiming beam. Subsequently, the controller 130 causes the lens driving sections 132 and 133 to move the lenses 123b and 151 in a predetermined direction (which may be either direction of each of the optical axes) by a predetermined amount whereby a change of the spot diameter can be recognized (S12). The image processing section 131 detects the spot diameter which varies with the movement of the lenses 123b and 151 and transmits the information (data) on the spot diameter to the controller 130. The controller 130 then compares the spot diameters between before and after the movement of the lenses 123b and 151. If the spot diameter after the lens movement is smaller than that before the lens movement (S13: YES), the controller 130 further moves the lenses 123b and 151 in the same direction as above (S14). If the spot diameter after the lens movement is larger (S13: NO), to the contrary, the controller 130 moves the lenses 123b and 151 in the reverse direction (S15).

The image processing section 131 detects the spot diameter of the aiming beam continuously and transmits the information (data) thereon to the controller 130. The controller 130 stops movements of the lenses 123b and 151 at the time when the spot diameter increases past the minimum value (S16: YES), and then moves the lenses 123b and 151 in the reverse direction to in S14 (for S13: YES) or in S15 (for S13: NO) to return them to the positions where the minimum value of the spot diameter is detected (S17). If NO in S16, on the other hand, the lenses 123b and 151 are moved in the same direction as in S14 (for S13: YES) or in S15 (for S13: NO) (S18).

If the moving direction and the moving amount of the lenses 123b and 151 are stored in relation to the information (data) of the image processing, the lenses 123b and 151 can be easily returned to the positions where the minimum spot diameter is detected. Using the above manner, the automatic sighting can be conducted.

In the above embodiment, the lenses 123b and 151 are moved interlockingly on respective optical axes. However, it is not so difficult for the operator to conduct sighting by manual operation while observing the affected part until the surroundings of the affected part is clearly observed. Accordingly, it is possible to move only the lens 123b without moving the lens 151.

In the above embodiment, the automatic sighting is conducted by movement of the lenses 123b and 151 in the respective optical axis directions. An alternative design is to provide a mechanism for electrically move the main unit 101 forward and backward whereby to execute the sighting by automatically moving the main unit 101 based on the information (data) obtained by the image processing.

In the apparatus of the second embodiment, as well as in the first embodiment, it may be arranged such that manual sighting is conducted by displaying the information (data) on the display, instead of the automatic sighting.

The automatic sighting switch may be provided on the head of the joystick instead of the control panel. In this case, the foot switch may also be used as a trigger switch. Moreover, it may be provided a selection switch for selecting use/nonuse of the automatic sighting.

With the laser treatment apparatus in the above embodiments, the operator can easily observe the patient's eye in a comfortable position. The apparatus can ensure accuracy and easiness in sighting to focus the treatment laser beam to the desired point.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A laser treatment apparatus for irradiating an affected part in the inside of a patient's eye with a treatment laser beam to treat the affected part, while allowing an operator to observe the affected part, including:
   treatment beam irradiation means including a first irradiation optical system for focusing the treatment laser beam on the inside of the patient's eye;
   aiming beam irradiation means including a second irradiation optical system for delivering an aiming beam into the patient's eye,
   the first irradiation optical system and the second irradiation optical system being optically adjusted such that sighting of the treatment laser beam in a direction of an optical axis with respect to the affected part is completed when the aiming beam forms a predetermined spot shape on the affected part in the inside of the patient's eye;
   sighting adjustment means for adjusting sighting of the aiming beam in a direction of an optical axis with respect to the affected part to adjust the sighting of the treatment laser beam, the sighting adjustment means including movement means for moving a sighting point of the second irradiation optical system in forward-and-backward directions of the optical axis direction;
   image pickup means including an image pickup optical system for imaging an area including the affected part in the inside of the patient's eye;
   sighting state detection means for detecting a spot image of the aiming beam from an image picked-up by the image pickup means to detect a sighting state of the aiming beam;
   movement detection means for detecting movement by the movement means;
   determination means for determining a direction of the optical axis direction in which the sighting point is to be moved based on results detected by the sighting state detection means and the movement detection means respectively; and
   movement control means for controlling the movement means based on the determined direction to complete the sighting.

2. The laser treatment apparatus according to claim 1, wherein the second irradiation optical system includes an optical system for delivering the aiming beam into the patient's eye so that the aiming beam focuses on a focus point of the treatment laser beam, and the sighting state detection means detects the sighting state based on one of a spot diameter and a size of the spot image of the aiming beam.

3. The laser treatment apparatus according to claim 1, wherein the treatment beam irradiation means includes a laser source which emits a YAG laser beam as the treatment laser beam.

4. The laser treatment apparatus according to claim 1, wherein the second irradiation optical system includes an optical system for delivering a plurality of aiming beams which are symmetrical about an optical axis into the patient's eye so that the aiming beams coincide with each other at a focus point of the treatment laser beam, and the sighting state detection means detects the sighting state based on at least one of an overlapping condition of the spot images of the plurality of aiming beams and a size of overlapped spot images.

5. The laser treatment apparatus according to claim 1, further including:
   an input switch for inputting a signal for starting automatic sighting, wherein the movement control means controls the movement means to move the sighting point by a predetermined amount in a predetermined direction of the optical axis direction based on the input signal for starting the automatic sighting.

6. The laser treatment apparatus according to claim 1, wherein a central axis of the first irradiation optical system is made coaxial with a central axis of the second irradiation optical system.

7. The laser treatment apparatus according to claim 1, wherein the movement means includes lens movement means for moving a lens provided in the second irradiation optical system in the forward-and-backward directions of the optical axis direction, wherein the movement detection means detects movement by the lens movement means, and wherein the movement control means controls the lens movement means based on the determined direction.

8. The laser treatment apparatus according to claim 1, further including:
   an input switch for inputting a signal for starting automatic sighting; and
   precluding means for precluding irradiation of the treatment laser beam to the affected part until the sighting is completed, wherein the signal for starting the automatic sighting is input even when a trigger signal for irradiating the treatment laser beam is input.

9. The laser treatment apparatus according to claim 1 further including observation means including a display for displaying the image picked up by the image pickup means on the display.

10. The laser treatment apparatus according to claim 9 further including display control means for causing the display to display a determination result by the determination means.

11. The laser treatment apparatus according to claim 9, wherein the display is place-changeable mounted on the apparatus.

* * * * *